United States Patent [19]

Durst et al.

[11] Patent Number: 4,567,253

[45] Date of Patent: Jan. 28, 1986

[54] 2-SUBSTITUTED DERIVATIVES OF PODOPHYLLOTOXIN AND ETOPOSIDE

[76] Inventors: Tony Durst, 1956 Sharel Dr., Ottawa, Canada, K1H 6W2; Margaret B. Glinski-Oomen, 3-242 Charlotte St., Ottawa, Canada, K1N 8L3; James C. Freed, 9 Centre St., Ovest, Aylmer, Canada, J9H 3A4

[21] Appl. No.: 576,981

[22] Filed: Feb. 3, 1984

[51] Int. Cl.[4] .................. C07H 15/20; C07D 317/44
[52] U.S. Cl. .................................. 536/18.1; 549/298
[58] Field of Search ................. 536/18.1, 6.4; 549/298

[56] References Cited

U.S. PATENT DOCUMENTS 4,413,120 11/1983 Whistler ............................. 536/6.4

OTHER PUBLICATIONS

Gensler, Walter J., et al., "Nonenolizable Podophyllotoxin Derivatives", Journal of Medicinal Chemistry, 20, No. 5, pp. 635–644, (1977).
Partridge et al., "Jour. of the American Chemical Society", 95, Jan. 2, 1973.

Primary Examiner—Johnnie R. Brown

[57] ABSTRACT

One aspect of this invention relates to 2-substituted podophyllotoxin corresponding to the formula:

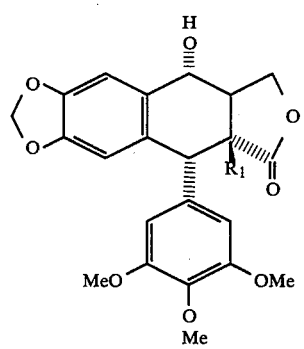

where $R_1$ is the residue of an electrophile reactant with the precursor enolate, e.g., halogen, i.e., Br, Cl, F and I, lower alkyl (preferably methyl), hydroxyl, —$SR_5$ where $R_5$ is lower alkyl, aralkyl or aryl and $COOR_6$ where $R_6$ is hydrogen or lower alkyl. Another aspect of this invention relates to 2-substituted etopsides and related compounds corresponding to the formula:

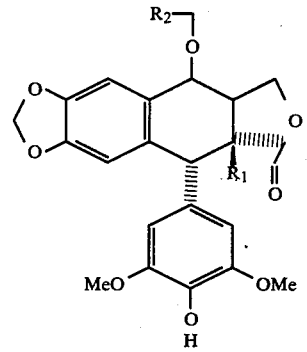

where $R_1$ is as defined above, and where $R_2$ is:

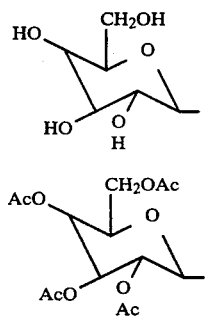

where AcO is acetyl; or

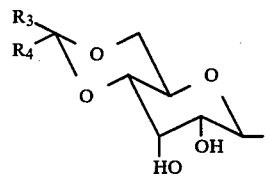

where $R_3$ is hydrogen and $R_4$ is alkyl, alkenyl, cycloalkyl, 2-furyl, 2-thienyl, aryl, aralkyl, or alkenyl wherein the aromatic ring (preferably phenyl) may be optionally substituted by one or more hydroxyl, alkyl, alkoxy, nitro or halogen; or where each of $R_3$ and $R_4$ is alkyl or where each of $R_3$ and $R_4$ taken together with the carbon atom to which they are attached signify a saturated cycloaliphatic ring having 5 or 6 carbon atoms; each alkyl, alkenyl or alkoxy above having no more than 10 carbon atoms and each aryl containing no more than 16 carbon atoms excluding substituent on the ring which are defined above. Yet another aspect of this invention relates to novel intermediate compounds. In addition, a further aspect of this invention relates to various methods for preparing the above compounds.

6 Claims, No Drawings

2-SUBSTITUTED DERIVATIVES OF PODOPHYLLOTOXIN AND ETOPOSIDE

BACKGROUND OF THE INVENTION

*Podophyllum peltatum linnaeus* (family: Berberidaceae; common names; Ray Apple, American Mandrake, Indian Apple, Wild Lemon, Duck's Foot) is an indigenous North American herbaceous perennial flowering in May. The Indians knew of its properties as a cathartic, anthelmintic and as a poison.

Podophyllin was included in the fourth edition of the United States Pharmacopoeia in 1863 but was dropped from the twelfth edition in 1942. The same year a report by Kaplan appeared that suggested podophyllin was very useful in clinical treatment of a type of venereal wart (*Condyloma acuminatum*), *New Orleans Med. Surg. J.*, 94: 388 (1942). Between the years 1940 to 1960, podophyllin was studied in many clinical conditions including diseases of the skin due to infectious agents, nonspecific dermatoses, gout, rheumatoid arthritis, benign and malignant growth, *J. Nat. Cancer Inst.*, 14: 967 (1954).

A great deal of effort by numerous investigators went into the isolation and identification of the components of podophyllin. In 1880 Podwyssotozki isolated a white crystalline substance which he named podophyllotoxin and which was believed to be the active component. By 1950 seventeen compounds had been isolated and characterized; four were flavonal pigments and the remainder were members of the lignan family. The structures of the compounds isolated are shown in Table 1.

TABLE 1

COMPOUNDS ISOLATED FROM PODOPHYLLIN

| NAME | # | $R_1$ | $R_2$ | $R_3$ |
|---|---|---|---|---|
| podophyllotoxin | 6 | OH | H | $CH_3$ |
| α-peltatin | 7 | H | OH | H |
| β-peltatin | 8 | H | OH | $CH_3$ |
| 4'-demethylpodophyllotoxin | 9 | OH | H | H |
| deoxypodophyllotoxin | 10 | H | H | $CH_3$ |
| podophyllotoxin glucoside | 11 | O—glucosyl | H | $CH_3$ |
| α-peltatin glucoside | 12 | H | O—glucosyl | H |
| β-peltatin glucoside | 13 | H | O—glucosyl | $CH_3$ |
| 4'demethylpodophyllo- | 14 | O—glucosyl | H | H |

TABLE 1-continued

COMPOUNDS ISOLATED FROM PODOPHYLLIN

| NAME | # | $R_1$ | $R_2$ | $R_3$ |
|---|---|---|---|---|
| picropodophyllotoxin | 15 | | | |
| tetradehydropodophyllotoxin | 16 | | | |
| sikkimotoxin | 17 | | | |
| quercetin | 18 | H | | OH |
| isorhamnetin | 19 | H | | $OCH_3$ |
| quercetin 3-galactoside | 20 | galactosyl | | OH |
| kaempferol | 21 | H | | H |

Podophyllotoxin has antimitotic activity by interacting with microtubules; [Kelly et al, *J. Nat. Cancer Inst.*, 14: 967 (1954); Comman et al, *Ann. N.Y. Acad. Sci.*, 51, 1443 (1952)]. It is also known that colchicine, 22 arrest cells in metaphase; Dustin, *Pharmacol. Rev.*, 15: 449 (1963).

4'-Dimethyl analogues of podophyllotoxin including 4'-demethylpodophyllotoxin, 4'-demethylepipodophyllotoxin, 4'-demethyldeoxypodophyllotoxin and α-peltatin induce the intracellular degradation of DNA in HeLa cells as well as affecting microtubule formation; Loike et al, *Biochemistry*, 15: 5443 (1976).

Kuhn and von Wartburg while studying methods of preparing podophyllotoxin glycosides developed a procedure for the preparation of epipodophyllotoxin glycosides which are epimeric to podophyllotoxin at $C_4$; *Helv. Chim. Acta.* 51: 163 and 1631 (1968) (Scheme 1).

SCHEME 1
PREPARATION OF
EPIPODOPHYLLOTOXIN GLYCOSIDES

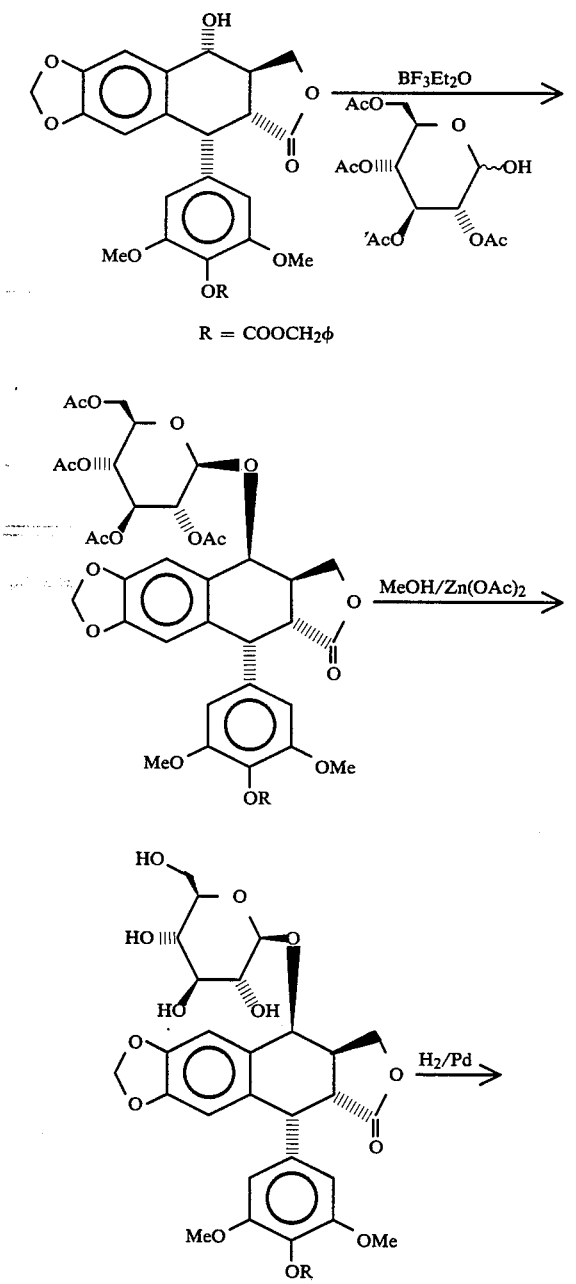

R = COOCH$_2\phi$

-continued
SCHEME 1
PREPARATION OF
EPIPODOPHYLLOTOXIN GLYCOSIDES

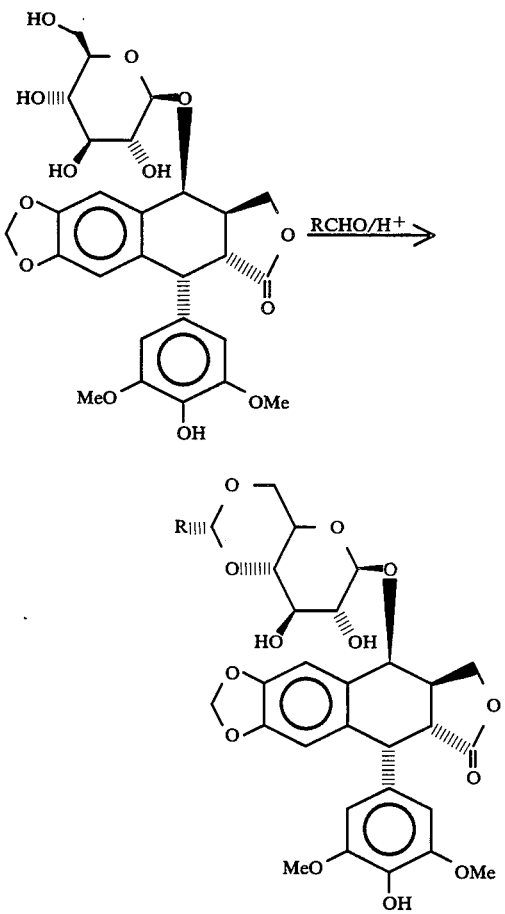

They prepared a variety of cyclic acetals of 4'-demethylepipodophyllotoxin B-glycoside and found that they exhibited not only a high activity in vitro but were much less toxic in in vivo testing against mouse lymphocytic leukemia (L-1210); Keller-Jerslen et al, *J. Med. Chem.*, 14: 936 (1971). Two of these derivatives were selected for clinical trials and proved to be very useful in treating a variety of cancers. These were 4'-demethyl-1-O-(4,6-O-ethylidene-β-D-glucopyranosyl)-epipodophyllotoxin, 24 (VP-16 or "Etoposide") and 4-demethyl-1-O-(4,6-O-(2-thenylidene)-β-D-glucopyranosyl)-epipodophyllotoxin, 25 (VM-26 or "Teniposide"). These agents are active in the treatment of a wide spectrum of cancers including bladder, small cell lung, ovarian, thyroid, breast, brain, soft tissue cancers, non-lymphocytic leukemia and Hodgkin's disease; Gensler et al, *J. Org. Chem.*, 31: 3224 (1966).

TABLE 2

| EFFECT OF CYCLIC ACETAL DERIVATIVES ON L-1210 LEUKEMIA | |
|---|---|
| R | MOUSE LEUKEMIA L-1210 % SURVIVAL TIME INCREASE |
| CH$_3$ 24 | 167 |
| CH$_2$CH$_3$ | 97 |

TABLE 2-continued
EFFECT OF CYCLIC ACETAL DERIVATIVES ON L-1210 LEUKEMIA

| R | MOUSE LEUKEMIA L-1210 % SURVIVAL TIME INCREASE |
|---|---|
| (furan) X = S 25 | 121 |
| X = O | 136 |
| $C_6H_5$ | 97 |
| $C_6H_5CH_2$ | 46 |
| 1-naphthyl | 95 |
| $CH_2CH=CH$ | 121 |
| $(CH_3)_3C$ | 57 |
| $p-FC_6H_4$ | 64 |
| $p-CH_3C_6H_4$ | 64 |

Stähelin showed that VM-26 and VP-16 prevent cells from entering mitosis and thus unlike the previously mentioned podophyllotoxin analogues they do not arrest cells in metaphase but in late S or $G_2$ phase of the cell cycle; Oncology, 35: 217 (1978). These compounds surprisingly possess a different mechanism of action other than inhibition of microtubule assembly. In fact, they have been shown not to bind to tubulin; Locke et al, Biochemistry, 15: 5435 (1976). A great deal of effort has gone into determining the exact mechanism of action of these compounds but to data there is no clear answer, although the point of action appears to be the interruption of DNA transcription. Very recent reports suggest that these agents interact with topoisomerase II, an enzyme involved in the uncoiling of DNA supercoils prior to transcription.

PREVIOUS SYNTHESIS OF PODOPHYLLOTOXIN

The first synthesis of podophyllotoxin, compound 6 (Scheme 2), was reported by Gensler and coworkers [J. Am. Chem. Soc., 76: 5894 (1954); J. Am. Chem. Soc., 76: 315 (1954)].

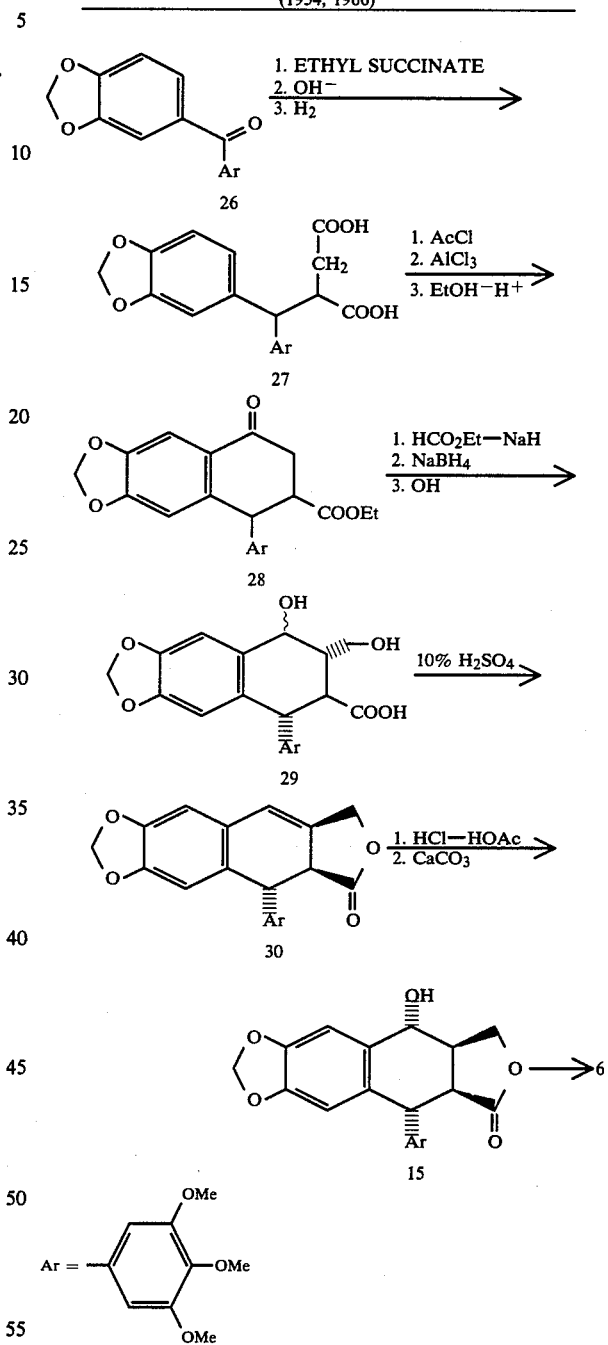

Stobbe condensation of 1-(3',4',5'-trimethoxybenzoyl)-3,4-methylenedioxybenzene 26 with ethyl succinate followed by saponification and hydrogenation gave the saturated dibasic acid 27. Conversion to the anhydride followed by intramolecular Friedel-Crafts acylation and then esterification gave the cyclic keto-ester 28. Condensation with ethyl formate followed by sodium borohydride reduction and saponification afforded the dihydroxy acid 29. Treatment with 10% aqueous sulfuric acid gave α-apopicropodophyllotoxin 30 which was converted to picropodophyllotoxin 15 by treatment with dry HCl in glacial acetic acid followed by aqueous calcium carbonate.

Podophyllotoxin epimerizes readily under basic conditions to picropodophyllotoxin. The reverse reaction has also been demonstrated so that equilibration affords a mixture containing a 97:3 ratio of picropodophyllotoxin to podophyllotoxin; Gensler et al, *J. Org. Chem.*, 131: 3224 (1966). Gensler avoided this thermodynamic limitation by treatment of 4-O-tetrahydropyranylpicropodophyllotoxin 31 with triphenylmethyl sodium to form the extremely rigid enolate which undergoes kinetic proton trapping with acetic acid to give a mixture of 55% picropodophyllotoxin and 45% podophyllotoxin (Scheme 3); *J. Org. Chem.*, 31: 4004 (1966).

SCHEME 4
KENDE'S SYNTHESIS OF PODOPHYLLOTOXIN (1981)

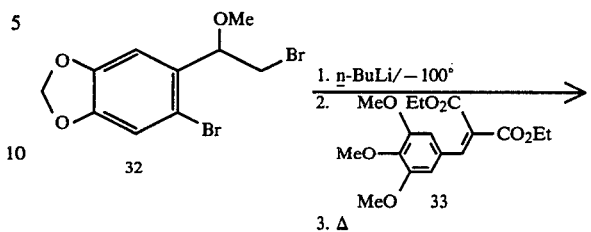

SCHEME 3

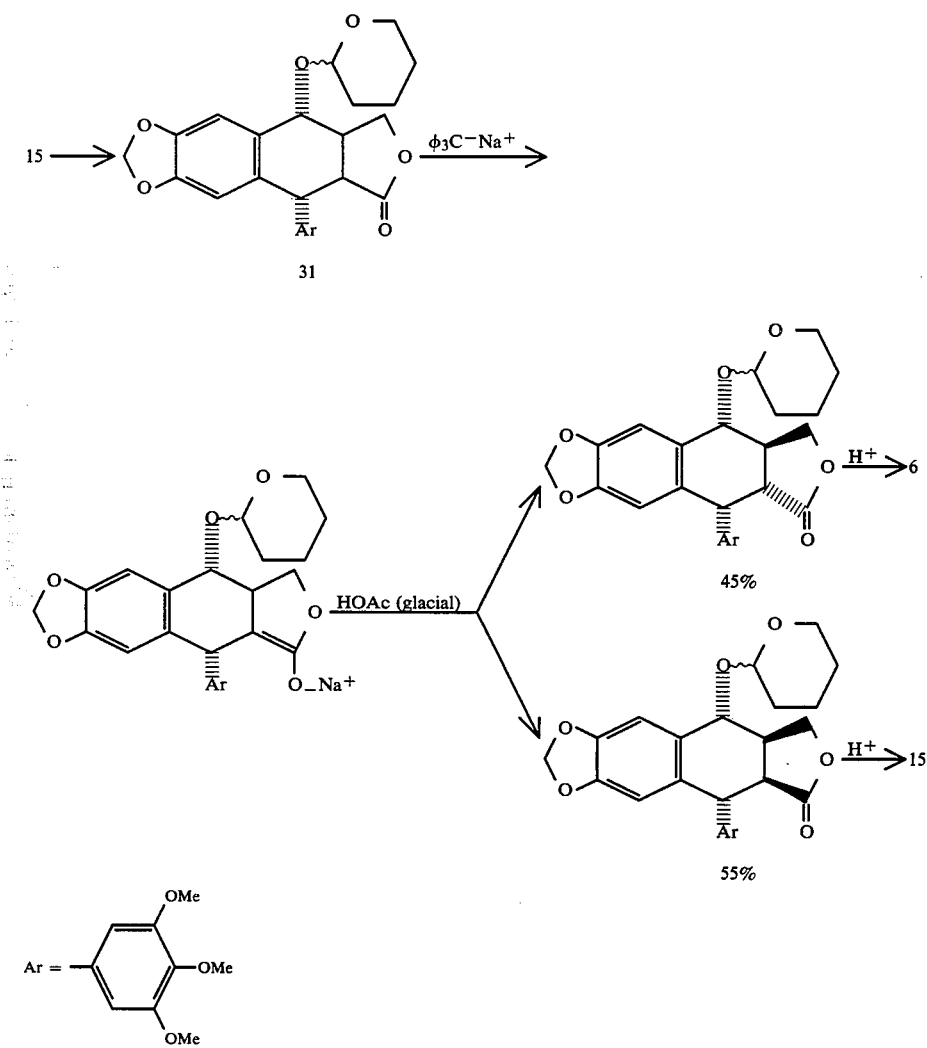

Kende has synthesized (±)-podophyllotoxin in 12 steps with an overall yield of 4.5% from piperonal *J. Am. Chem. Soc.*, 99: 7082 (1977); *J. Org. Chem.*, 40: 2828 (1981) (Scheme 4).

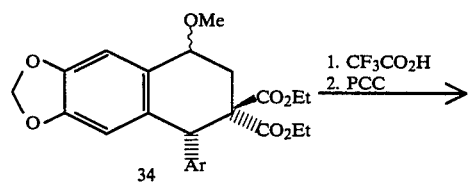

-continued
SCHEME 4
KENDE'S SYNTHESIS OF PODOPHYLLOTOXIN (1981)

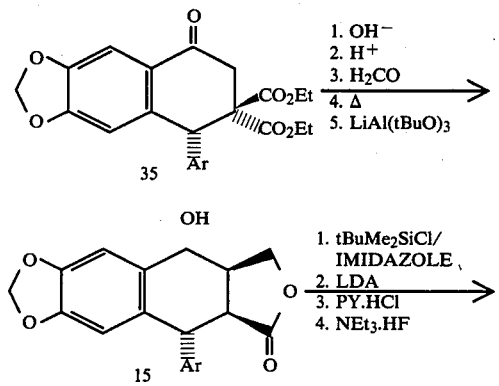

6 + 15 (1:1)

The methoxydibromide intermediate 32 was obtained by Wittig methylenation of piperonal followed by methoxybromination. Lithiation followed by condensation with the arylidene malonate derivative 33 and subsequent heating gave the diastereomeric mixture of aryl tetralin diesters 34 in a high yield. Solvolysis followed by oxidation gave the keto diester 35 which was converted to picropodophyllotoxin 15 by the following manipulations: saponification decarboxylation, formylation, retroaldol thermolysis and finally stereoselective reduction.

In an improvement of the Gensler epimerization, picropodophyllotoxin was converted to the t-butyldimethylsilyl ether. Formation of the enolate with LDA, irreversible quenching with pyridine hydrochloride followed by desilylation afforded 36% podophyllotoxin and 34% picropodophyllotoxin.

Rodrigo's synthesis of podophyllotoxin was the first scheme devised to avoid the formidable thermodynamic hurdle present in both the Gensler and Kende syntheses *J. Org. Chem.*, 45: 4538 (1980).

DESCRIPTION OF THE INVENTION

One aspect of this invention relates to 2-substituted podophyllotoxin corresponding to the formula:

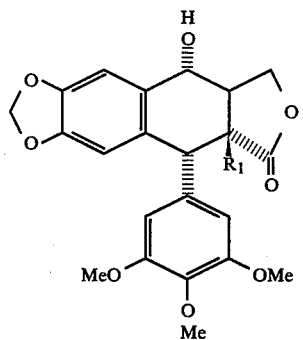

where $R_1$ is the residue of an electrophile reactant with the precursor enolate, e.g., halogen, i.e., Br, Cl, F and I, lower alkyl (preferably methyl), hydroxyl, —$SR_5$ where $R_5$ is lower alkyl, aralkyl or aryl and $COOR_6$ where $R_6$ is hydrogen or lower alkyl.

Another aspect of this invention relates to 2-substituted etopsides and related compounds corresponding to the formula:

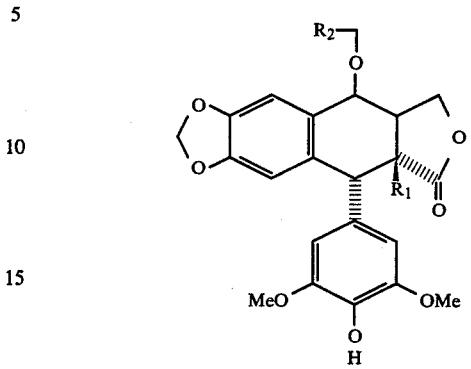

where $R_1$ is as defined above, and where $R_2$ is:

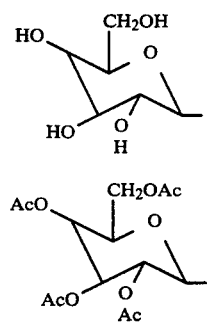

where AcO is acetyl, or

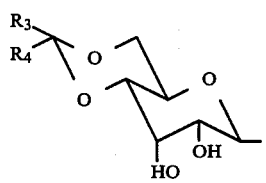

where $R_3$ is hydrogen and $R_4$ is alkyl, alkenyl, cycloalkyl, 2-furyl, 2-thienyl, aryl, or aralkyl wherein the aromatic ring (preferably phenyl) may be optionally substituted by one or more hydroxyl, alkyl, alkoxy, nitro or halogen; or
where each of $R_3$ and $R_4$ is alkyl; or where $R_3$ and $R_4$ taken together with the carbon atom to which they are attached signify a saturated cycloaliphatic ring having 5 or 6 carbon atoms; each alkyl, alkenyl or alkoxy above having no more than 10 carbon atoms and each aryl containing substructure containing no more than 16 carbon atoms excluding substituent on the ring which are as defined above. The compounds where $R_3$ and $R_4$ are hydrogen or where one of $R_3$ and $R_4$ is methyl and the other hydrogen are preferred.

Yet another aspect of this invention relates to novel intermediate compounds.

In addition, a further aspect of this invention relates to various methods for preparing the above compounds.

The epimerization of podophyllotoxin to picropodophyllotoxin is thought to occur under physiological conditions, Kocsis et al, Intern. Pharmacodyn, Ther., 111, 134 (1957); Kelly et al, Cancer Res., 11, 263 (1951);

Allen et al, Am. Assoc. Caner. Res. Proc., Abstr. No. 21 (1976). The biological activity of picropodophyllotoxin as well as other cis analogues is either much lower than that of the trans isomers or is negligible, Emmenegger et al, Arzneim. Forsch., 11 327, 459 (1978). It appears that epimerization may be the primary method of detoxification by the cell.

Gensler suggested that the low level activity observed for picropodophyllotoxin might be due to the small amounts of podophyllotoxin generated by equilibration, Gensler et al, J. Org. Chem., 31, 3224 (1966). It seems unlikely that under the neutral conditions of the tubulin binding assay that epimerization could occur since there have been no reports of an interconversion other than that by base.

Gensler modified this suggestion based on the results of 60 MHz and 360 MHz $^1$H nmr studies of both Ayres and Brewer, Ayres et al, J. Chem. Soc. Perkin I, 1343 (1972) and Brewer et al, J. Med. Chem., 22, 215 (1979).

Picropodophyllotoxin can exist with the trimethoxybenzene ring (E-ring) in an equatorial or quasi-axial conformation. Gensler proposed that the residual activity may be due to the minor, quasi-axial conformation which places the E-ring in approximately the same orientation found in podophyllotoxin.

From the chemotherapeutic point of view, the epimerization is undesirable, since limiting the physiological lifetime of the drug would set an upper limit to their biological effectiveness. Gensler decided to approach this problem by synthesizing derivatives in which epimerization was precluded. He was unable to replace the hydrogen at the C$_2$ position with a suitable substituent and retain the trans-fused γ-lactone. Treatment of 4-deoxypodophyllotoxin 10 with triphenylmethyl lithium produced the enolate 138 which was carboxylated with carbon dioxide to give 2-carboxydeoxypicropodophyllotoxin 139, Gensler et al, J. Med. Chem. 20, 635 (1977).

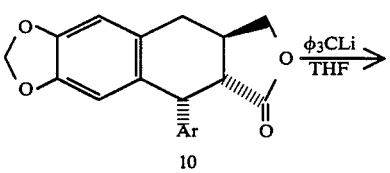

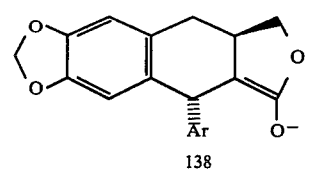
138

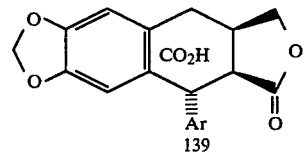
139

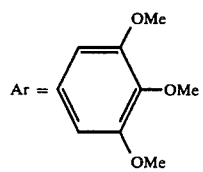

Gensler turned his attention towards blocking the enolization mechanism by eliminating the lactone group altogether. He prepared a series of "delactonized" derivatives 140 in which the carbonyl group has been reduced to methylene and the lactone oxygen was replaced by a variety of functions: S, SO$_2$, CO and CH$_2$, Gensler et al, J. Med. Chem., 20, 635 (1977). None of these compounds proved to more effective than podophyllotoxin or deoxypodophyllotoxin, Loike et al, Cancer. Res., 38, 2688 (1978).

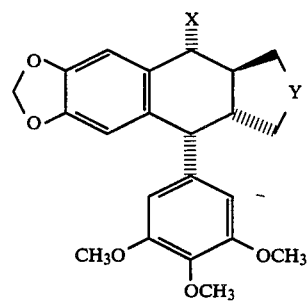
140

X = H, OH.
Y = O, S, SO$_2$, CO, CH$_2$.

It was decided to reinvestigate the problem of synthesizing C$_2$-substituted podophyllotoxin derivatives via the enolate anion. The dianion 141 of podophyllotoxin was prepared by treatment of podophyllotoxin 6 with two equivalents of LDA at −78 in dry THF. The enolate was reacted with excess methyl iodide at −78°, warmed to room temperature and stirred for an additional 18 h. Normal workup and HPLC (hexanes/ethyl acetate, 1:1) furnished a 3:1 mixture of 2-methylpicropodophyllotoxin 142 and 2-methylpodophyllotoxin 143, respectively, in an overall yield of 71%. Thus, under these conditions the desired product 143 (the one retaining the trans-lactone) was obtained as the minor component.

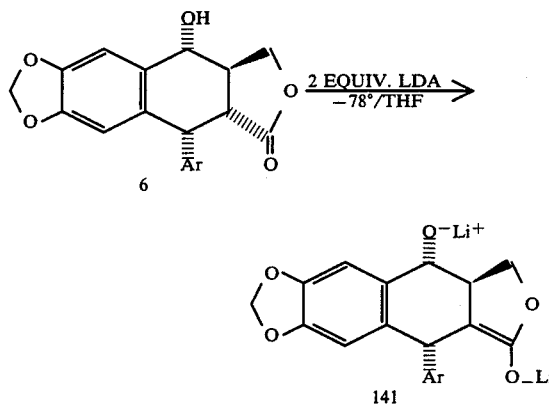

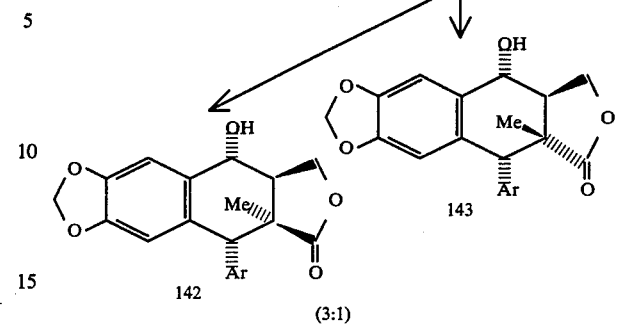

The following nomenclature has been adopted herein for the substituted derivatives of podophyllotoxin. Derivatives having the same stereochemistry at carbons 2 and 3 as podophyllotoxin are named as being derived from the same. Similarly, derivatives having the same stereochemistry at carbons 2 and 3 as picropodophyllotoxin are named as being derived from picropodophyllotoxin.

Since Gensler had obtained better results with protein trapping of the 4-O-tetrahydropyranylpodophyllotoxin enolate anion than with the dianion attention, was turned to this route (Scheme 26). Treatment with dihydropyran in the presence of TsOH converted podophyllotoxin to 4-O-tetrahydropyranylpodophyllotoxin 144 in good yield.

The enolate 145 was formed by treatment of 144 with 1.1 equivalents LDA at −78° in dry THF. Trapping of the enolate with methyl iodide (−78° to rt, 18 h) gave after workup a mixture of tetrahydropyranyl derivatives. The crude

SCHEME 5

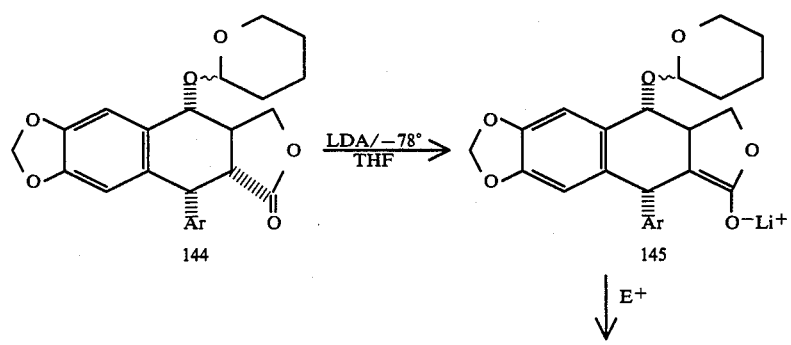

SCHEME 5

-continued

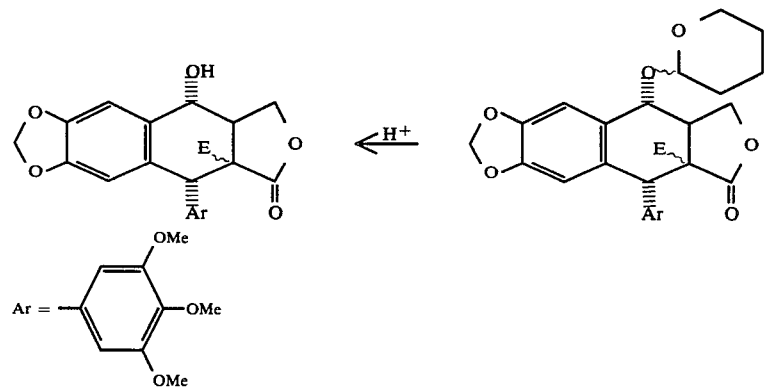

product was exposed directly to the action of aqueous acid to remove the protecting group. Normally the $C_2$ substituted tetrahydropyranyl derivatives were not isolated because of the added complication due to the presence of additional diastereomers caused by the tetrahydropyranyl ring. HPLC (hexanes/ethyl acetate, 1:1) effected a clean separation and afforded 2-methylpodophyllotoxin 143 and 2-methylpicropodophyllotoxin 142 in yields of 43 and 19%, respectively.

Similarly, treatment of the enolate 145 with dry oxygen for 30 minutes at −78° followed by reduction of the intermediate hydroperoxides with aqueous sodium sulfite gave after removal of the tetrahydropyranyl group a 1:1 inseparable mixture of 2-hydroxypodophyllotoxin 146 and 2-hydroxypicropodophyllotoxin 147 in 84% yield. This difference in stereochemical outcome can be explained on the basis of mechanistic differences in the reaction of carbanions with alkyl halides and with oxygen. The latter reaction is an electron transfer process involving a radical intermediate, Buncel et al., *Comprehensive Carbanion Chemistry*, Part A, Elsevier, Amsterdam, page 202 (1980).

The best stereochemical result was obtained with chlorination of the enolate 145 by reaction with excess hexachloroethane (−78° to rt, 18 h) where only one product was obtained after removal of the protecting group. Chromatography (hexanes/ethyl acetate, 1:1) afforded 2-chloropodophyllotoxin 148 in 74% yield. In this case the tetrahydropyranyl derivative was also isolated and characterized. 2-Chloro-4-O-tetrahydropyranylpodophyllotoxin 149 was obtained as a 3:2 mixture of diastereomers (due to the presence of a chiral center in the THP portion) after precipitation from ether/hexanes. The mass spectrum and 360 MHz $^1$H nmr spectrum of 149 are consistent with their structure. The results of the enolate trapping experiments are summarized in Table 3.

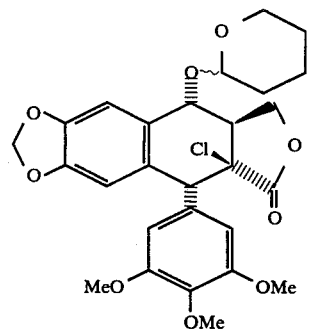

149
3:2 MIXTURE OF DIASTERIOMERS

TABLE 3

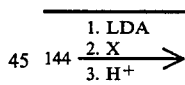

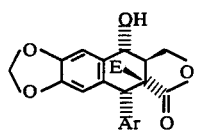 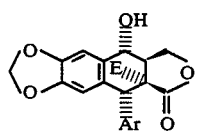

| | E = CH₃ 143 | E = CH₃ 142 |
|---|---|---|
| | OH 146 | OH 147 |
| | Cl 148 | |

| X | E | PRODUCTS AND YIELDS | RATIO PODO/PICRO |
|---|---|---|---|
| CH₃I | CH₃ | 143 (43%) 142 (18%) | 2.4/1 |
| O₂ | OH | 146 + 147 (84%) | 1/1 |
| Cl₃CCCl₃ | Cl | 148 (74%) | — |

PROPOSED M.S. FRAGMENTATION PATHWAY FOR 149

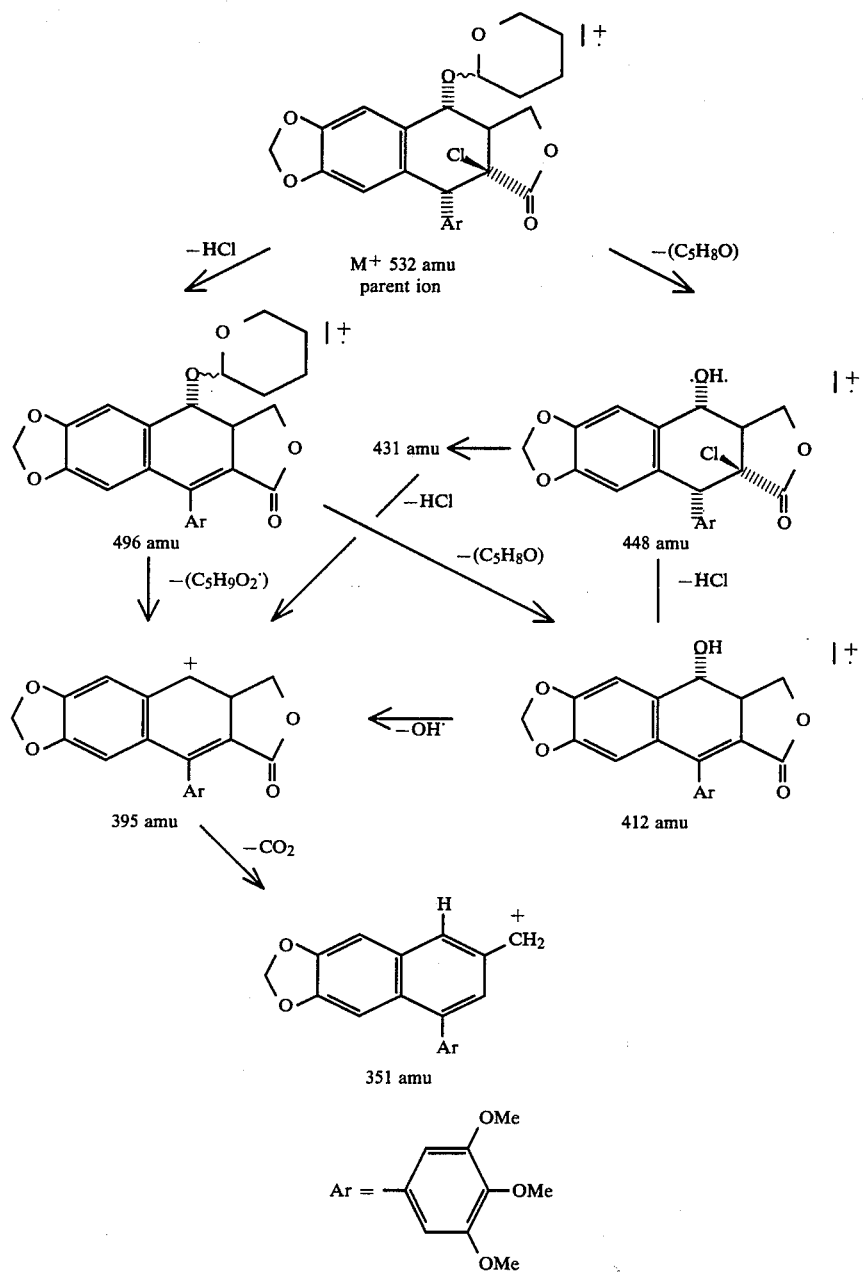

The structures of the $C_2$-substituted podophyllotoxin derivatives were assigned on the basis of their 360 MHz $^1H$ nmr spectra. The nmr data for these compounds are summarized in Tables 4 and 5. Substitution at $C_2$ was clearly evident by the presence of a sharp singlet for $H_1$ at 4.26 ppm, 4.23 ppm and 4.79 ppm, in 143, 142 and 148, respectively.

The stereochemistry at $C_2$ was assigned on the basis of the values of the coupling constants $J_{H3-H11}$ and $J_{H3-H11}$. The numerical values for the constants are lower in picropodophyllotoxin ($J_{H3-H11}=1.5$ Hz and $J_{H3-H11}=6.0$ Hz) than in podophyllotoxin ($J_{H3-H11}=9.0$ Hz and $J_{H3-H11}=8.0$ Hz, Brewer et al, J. Med. Chem., 22, 215 (1979).

The aromatic protons show a characteristic three signal pattern in the nmr which is dependent on the stereochemistry of the lactone ring. It was observed that in the trans (podo) series the two singlets for the methylenedioxybenzene protons ($H_5$ and $H_7$) were consistently downfield from the two proton singlet representing the trimethoxybenzene protons ($2\times H_8$). The chemical shifts for $H_5$, $H_7$ and $H_8$ were 7.11, 6.51, 6.37 (podophyllotoxin); 7.10, 6.48, 6.36 (2-methylpodophyllotoxin); 7.09, 6.49, 6.44 (2-chloropodophyllotoxin) and 7.10, 6.49, 6.38 (2-hydroxypodophyllotoxin). In the cis (picro) series the two proton singlet for the trimethoxybenzine protons was slightly downfield from the $H_7$ signal. The observed chemical shifts for $H_5$, $H_8$ and $H_7$ were 7.05, 6.45, 6.38 (piceopodophyllotoxin); 6.76, 6.78, 6.65 (2-methylpicropodophyllotoxin) and 7.04, 6.45, 6.38 (2-hydroxypicropodophyllotoxin).

¹H NMR DATA FOR THE 2-SUBSTITUTED PODOPHYLLOTOXIN DERIVATIVES

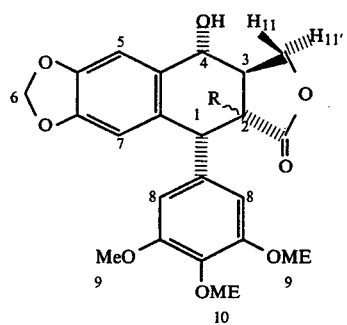

All other data collected for compounds 142, 143, 146, 147 and 148 were in agreement with the assigned structures.

Biological testing against either Leukemia L1210 or P388 was performed on the $C_2$ substituted derivatives (142, 143, 146, 147 and 148) at the antitumour division of Bristol Laboratories, Syracuse, N.Y. The general testing protocol was as follows, Geran et al, Cancer Chemotherapy Reports, Part 3, Vol. 3, No. 2, 1–87 (1972). Ascitic fluid containing $10^6$ cells was implanted intraperitonealy in female $CDF_1$ mice (six mice per test group). Treatment began 24 hours after implant and the parameter was median survival time. Results are given as percent increased survival time of test group over control group (% T/C). An initial $T/C \geq 125$ is considered significant antitumour activity.

The results are shown in Tables 6 and 7. The methyl derivatives 142 and 143 were inactive both in the L1210 and P388 tests. The mixture of hydroxyl derivatives 146 and 147 was toxic, having a T/C of less than 85, as was podophyllotoxin itself under the testing conditions. Interestingly, 2-chloropodophyllotoxin 148 had a level of antitumour activity against P388 substantially above the accepted significant level (T/C=156).

TABLE 4

| | CHEMICAL SHIFTS | | | | | | | | | | | |
|---|---|---|---|---|---|---|---|---|---|---|---|---|
| COMPOUND | $H_1$ | $H_3$ | $H_4$ | $H_5$ | $H_6$ | $H_{6'}$ | $H_7$ | $H_8$ | $H_9$ | $H_{10}$ | $H_{11}$ | $H_{11'}$ |
| 6 | 4.59 | 2.77 | 4.77 | 7.11 | 5.98 | 5.98 | 6.51 | 6.37 | 3.75 | 3.81 | 4.09 | 4.60 |
| 143 | 4.26 | 2.89 | 4.70 | 7.10 | 5.97 | 5.98 | 6.48 | 6.36 | 3.75 | 3.81 | 4.17 | 4.51 |
| 148 | 4.79 | 3.07 | 4.98 | 7.09 | 5.97 | 5.99 | 6.49 | 6.44 | 3.77 | 3.84 | a | a |
| 146 | a | a | a | 7.10 | a | a | 6.49 | 6.38 | 3.74 | 3.83 | a | a |
| 147 | a | a | a | 7.04 | a | a | 6.34 | 6.46 | 3.79 | 3.87 | a | a |
| 15 | 4.11 | 2.79 | 4.51 | 7.05 | 5.94 | 5.94 | 6.38 | 6.45 | 3.78 | 3.85 | 4.44 | 4.53 |
| 142 | 4.23 | 2.79 | 4.57 | 6.76 | 5.94 | 5.96 | 6.65 | 6.78 | 3.79 | 3.80 | a | a | a—not measurable with accuracy

TABLE 5

| | COUPLING CONSTANTS | | | | |
|---|---|---|---|---|---|
| COMPOUND | $J_{H3-H4}$ | $J_{H3-H11}$ | $J_{H3-H11'}$ | $J_{H11-H11'}$ | $J_{H6-H6'}$ |
| 6 | 9.1 | 9.0 | 8.0 | 8.8 | 0.5 |
| 143 | 11.0 | 10.5 | 7.5 | 9.0 | 0.5 |
| 148 | 9.5 | 9.0 | 7.0 | a | 0.5 |
| 15 | 8.3 | 1.5 | 6.0 | 10.2 | 0.5 |
| 142 | 7.8 | 1.4 | 6.0 | a | 0.5 |

TABLE 6

| EFFECT OF PODOPHYLLOTOXIN DERIVATIVES ON P388 LEUKEMIA | | | | | | |
|---|---|---|---|---|---|---|
| MATERIAL | TREATMENT SCHEDULE | DOSE IP mg/kg/inj | MST DAYS | EFFECT MST % T/C | AWC gm d.6 | SURVIVORS DAY 5 |
| NSC 38270 | d.1–5 | 0.8 | 13.0 | 144 | −0.5 | 6/6 |
| | | 0.4 | 12.5 | 139 | −0.6 | 6/6 |
| VP-16 (24) | d.1 & 5 | 40 | >30.0 | >333 | −1.8 | 6/6 |
| | | 20 | >30.0 | >333 | −1.7 | 6/6 |
| VM-26 (25) | d.1 & 5 | 40 | >30.0 | >333 | −1.4 | 6/6 |
| | | 20 | 26.0 | 289 | −0.6 | 6/6 |
| 143 | d.1 & 5 | 120 | 9.0 | 100 | +1.8 | 6/6 |
| | | 60 | 8.0 | 89 | +2.7 | 6/6 |
| | | 40 | 8.5 | 94 | +2.2 | 6/6 |
| | | 20 | 8.0 | 89 | +2.4 | 6/6 |
| | | 10 | 8.0 | 89 | +3.5 | 6/6 |
| | | 5 | 9.0 | 100 | +3.3 | 6/6 |
| 146 & 147 | d.1 & 5 | 80 | TOX | TOX | TOX | 2/6 |
| | | 40 | TOX | TOX | TOX | 3/6 |
| | | 20 | 10.0 | 111 | −0.9 | 6/6 |
| | | 10 | 9.0 | 100 | −0.1 | 6/6 |
| 148 | d.1 & 5 | 40 | 14.0 | 156 | −2.8 | 5/6 |
| | | 20 | 11.0 | 122 | −1.0 | 5/6 |
| | | 10 | 9.0 | 100 | +0.6 | 6/6 |
| | | 5 | 9.0 | 100 | 0 | 6/6 |
| PODOPHYLLO-TOXIN 6 | d.1 & 5 | 60 | TOX | TOX | TOX | 0/6 |
| | | 30 | TOX | TOX | TOX | 1/6 |
| | | 15 | 10.0 | 111 | −0.1 | 6/6 |
| | | 7.5 | 10.0 | 111 | +0.7 | 6/6 |

TABLE 6-continued
EFFECT OF PODOPHYLLOTOXIN DERIVATIVES ON P388 LEUKEMIA

| MATERIAL | TREATMENT SCHEDULE | DOSE IP mg/kg/inj | MST DAYS | EFFECT MST % T/C | AWC gm d.6 | SURVIVORS DAY 5 |
|---|---|---|---|---|---|---|
| CONTROL | | SALINE | 9.0 | 100 | −0.5 | 10/10 |

Tumor inoculum: $10^6$ ascites cells implanted ip.
Host: $CDF_1$ female mice.
TOX: <4/6 mice alive on Day 5.
Evaluation: MST = median survival time.
Effect: % T/C = (MST treated/MST control) × 100
Criteria: % T/C > or = 125 considered significant antitumor activity.

TABLE 7
EFFECT OF PODOPHYLLOTOXIN DERIVATIVES ON LEUKEMIA L1210

| MATERIAL | TREATMENT SCHEDULE | DOSE IP mg/kg/inj | MST DAYS | EFFECT MST % T/C | AWC gm d.6 | SURVIVORS DAY 5 |
|---|---|---|---|---|---|---|
| VP-16 | d.1 & 5 | 45 | 20.0 | 286 | −2.8 | 6/6 |
| | | 30 | 18.0 | 257 | −3.1 | 6/6 |
| 142 | d.1 & 5 | 45 | 7.0 | 100 | +0.7 | 6/6 |
| | | 30 | 7.0 | 100 | +0.2 | 6/6 |
| | | 15 | 7.0 | 100 | +0.9 | 6/6 |
| | | 7.5 | 7.0 | 100 | +0.5 | 6/6 |
| 142 & 143 | d.1 & 5 | 60 | 7.0 | 100 | −1.0 | 6/6 |
| | | 45 | 7.0 | 100 | +0.2 | 6/6 |
| | | 30 | 7.0 | 100 | +1.0 | 6/6 |
| | | 15 | 6.0 | 86 | +1.0 | 6/6 |
| CONTROL | | saline | 7.0 | — | +0.6 | 10/10 |

TABLE 8
EFFECT OF VP-16 DERIVATIVES ON LEUKEMIA P388

| MATERIAL | TREATMENT SCHEDULE | DOSE IP mg/kg/inj | MST DAYS | EFFECT MST % T/C | AWC gm d.6 | SURVIVORS DAY 5(45) |
|---|---|---|---|---|---|---|
| VP-16 | d.1 & 5 | 40 | >45.0 | >500 | −2.2 | 6/6 (4) |
| | | | >45.0 | >500 | −1.4 | 6/6 (4) |
| 150 | d.1 & 5 | 60 | >45.0 | >500 | −1.8 | 6/6 (5) |
| | | 30 | 29.0 | 322 | −1.2 | 6/6 (2) |
| | | 15 | 21.4 | 239 | −1.0 | 6/6 |
| | | 7.5 | 16.0 | 178 | −0.3 | 6/6 |
| CONTROL | | saline | 9.0 | — | −0.5 | 10/10 |

Tumor inoculum: $10^6$ ascites cells implanted ip.
Host: $CDF_1$ female mice.
Evaluation: MST = median survival time.
Effect: % T/C = (MST treated/MST control) × 100.
Criteria: % T/C > or = 125 considered significant antitumor activity.

Encouraged by the promising result with the chloroderivative and being aware that the glycoside moiety, as found in VP-16 (etoposide), might yield lower toxicity and high activity, it was decided to prepare the 2-chloro derivative of VP-16 (Scheme 6). Treatment of 4′-demethyl-1-O-(4,6-O-ethylidene-β-D-glucopyranosyl)-epipodophyllotoxin 24 (VP-16) with four equivalents of LDA at −78° in dry THF produced a pale yellow suspension. Excess hexachloroethane was added and the mixture warmed very slowly to room temperature and stirred for an additional 18 h. Normal workup and PTLC (hexanes/ethyl acetate, 1:3) afforded 2-chloro-4′-O-demethyl-1-O-ethylidene-βglucopyranosyl) epipodophyllotoxin 150, albeit in only 10% yield. The remaining product was starting material. The low yield is believed to be due to the insolubility of the polyanion under the reaction conditions of −78° with THF as the solvent. The yield may be improved by the use of polar co-solvents such as HMPT. The 360M Hz $^1$H nmr spectrum and mass spectrum of 150 are consistent with their structure.

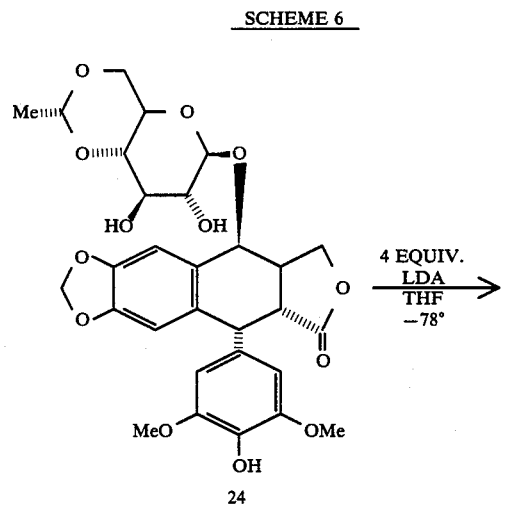

SCHEME 6

4 EQUIV. LDA / THF −78°

24

-continued
SCHEME 6
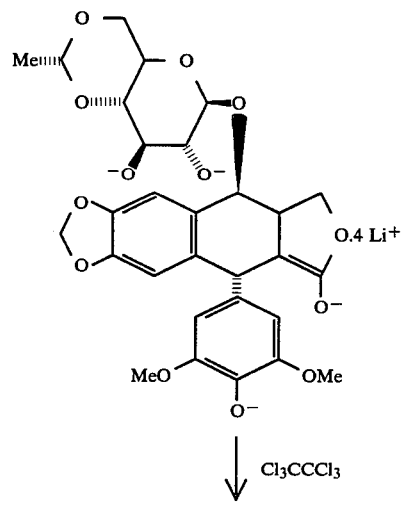
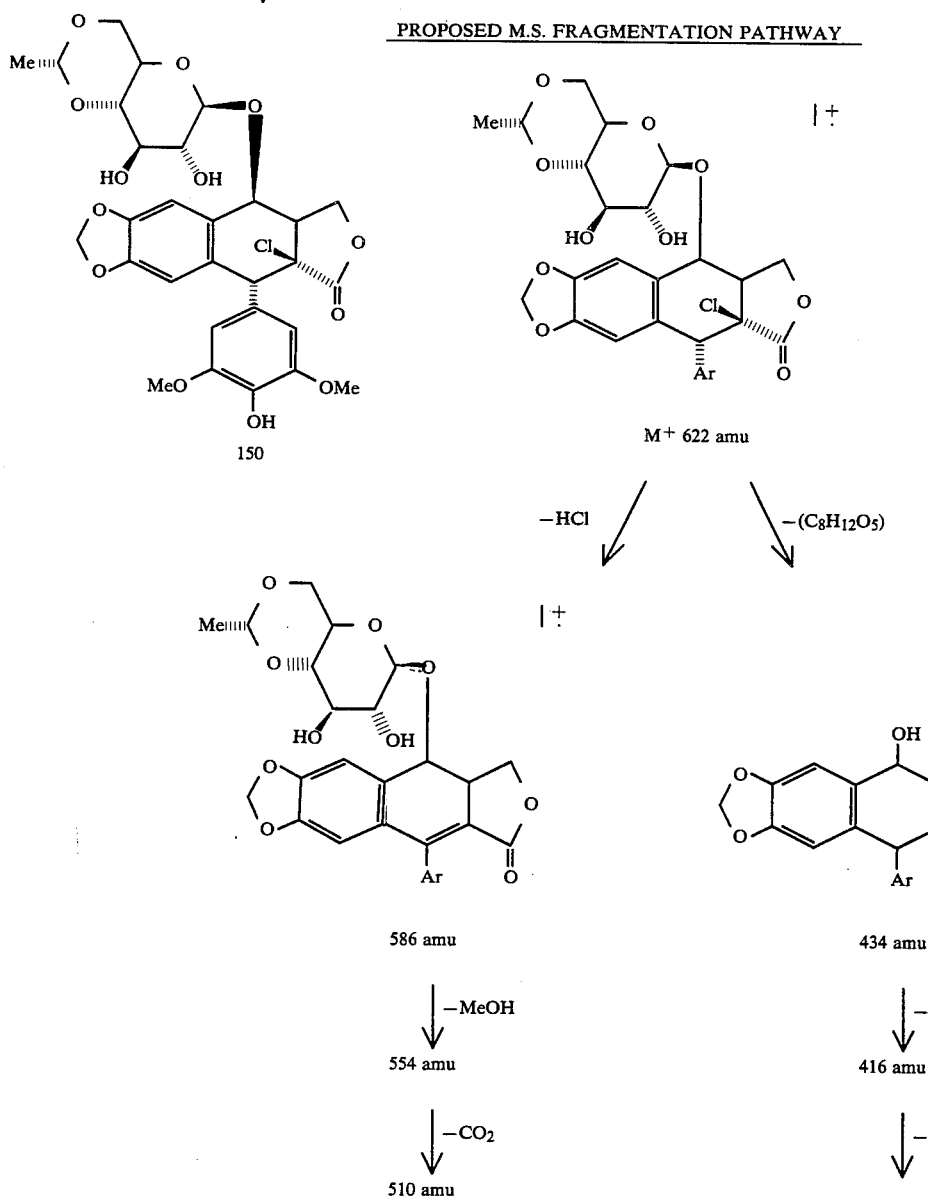
PROPOSED M.S. FRAGMENTATION PATHWAY
150
$M^+$ 622 amu
−HCl
−($C_8H_{12}O_5$)
586 amu
434 amu
−MeOH
−$H_2O$
554 amu
416 amu
−$CO_2$
−HCl
510 amu -continued
PROPOSED M.S. FRAGMENTATION PATHWAY

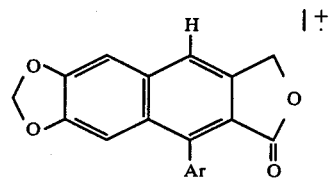

PARENT ION 380 amu

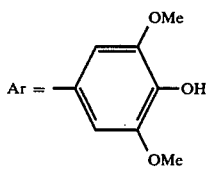

As can be seen from the above a simple method for preparing noneolisable podophyllotoxin derivatives which still contain the vitally important trans γ-lactone moiety has been discovered. This route has led to the preparation of 2-chloro derivatives which have a high activity in the Leukemia P388 tests. The 2-chloro VP-16 derivative appears to be a better agent than VP-16, the currently used clinical agent. This scheme can be used to introduce a wide variety of substituents at $C_2$ in both the podophyllotoxin and podophyllotoxin glycoside series.

Thus, broadly a process of forming the podophyllotoxin and Etoposide like derivatives of this invention comprises forming an enolate of the precursor compound (i.e. the final compound without the 2- substituent

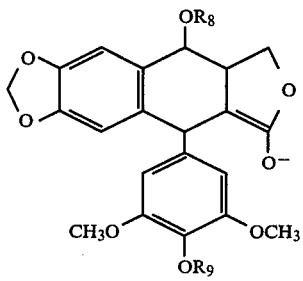

where $OR_8$ is $O^-$ or where $R^8$ is $R_2$ as defined above, or an anion or polyanion thereof where appropriate, or a base stable protecting group (the latter formed by blocking the corresponding hydroxyl group of podophyllotoxin prior to enol formation) and $OR_9$ is methoxy or $O^-$ and then quenching the enolate with at least about an equivalent amount of an electrophile (and, where present, removing the base stable protecting group) to form the desired Formulas I or II, supra.

The enolate is formed in an inert solvent, for example, tetrahydrofuran (THF) or dimethoxyethane by reacting the precursor compound with a non-nucleophic base, for example, lithium diisopropyl amide, at a low anion stabilizing temperature, for example about −78° C., to form the corresponding anion or polyanion; for example, a dianion in the case of podophyllotoxin and a tetraanion in the case of Etoposide.

The resultant enolate is then quenched with an electrophile capable of reacting with the enolate to form 2-substituted corresponding to the Formulas I and II, above. The quenching reaction is conducted at a reaction promoting temperature preferably about 0° C. Presently, the electrophile in about molar amounts or in slight excess (for example up to 25% excess) is added to the cold stable anion solution and the solution allowed to warm to about 0° C. or higher to promote the reaction. Examples of suitable electrophiles include a positive halogen source which halogenates the 2 position, for example, hexachloroethane or chlorine, sulfuryl chloride ($SO_2Cl_2$) or N-chlorosuccinamide, or for example, other suitable positive bromine, fluorine or iodine sources; an alkylating agent which alkylates the 2-position such as primary alkyl iodides or bromides such as, for example, methyl iodide; dry oxygen which hydroxylates the 2 position; or other 2-substituent generating agents such as alkyl- or aryl-disulfides or thiolsulfonates; and chloroformates or chlorocarbonates such as $CO_2C_2H_5$.

Where the reaction between the enolate and the electrophile is difficult, it is sometimes preferred to employ a minor amount, preferably up to 20%, of a co-solvent such as hexamethylphosphoramide and/or to conduct the reaction at slightly higher temperatures in order to complete the reaction.

The 2-β substituted compounds are the compounds which demonstrate antitumor activity. In at least some cases the product of the electrophilic reaction is a mixture of the 2-α and 2-β isomers. Where this occurs the mixture can be employed as an antitumor agent or the mixture can be separated by techniques known in the art to provide the pure-2-β isomer. It has been discovered that the use of a base stable protecting group on the hydroxyl group of podophyllotoxin enhances the formation of the -2-β isomer. Thus, generally formation of the 2-β isomer increases as follows:

$O^-$ < THP < silyl ether e.g. t-butyldimethyl silyl, diphenylmethyl silyl.

In yet another variant of the above described processes, the enolate related to the compounds of Formula I can be converted into the enol silyl ether

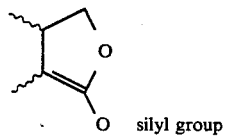

for example with the silyl group as SiCH₃ or Si(CH₃)₂tC₄H₉ by reacting the enolate group with at least about an equivalent of the appropriate silyl chloride. Subsequent reaction of the enol silyl ether with an electrophile in the manner described above for the enolate reaction yields the compounds of Formula I.

Still yet another method of forming the compounds of Formula II comprises first forming a compound of Formula I above and then adding R₂ to said compound to form the compound of Formula II. Methods for adding the R₂ group to podophyllotoxin are known in the art; see for example, U.S. Pat. Nos. 3,408,441 and 3,524,844. These processes are equally adaptable for adding the R₂ group to the compounds of Formula I.

A number of compounds of Formulas I and II have been shown to possess cytotoxic activity against tumors in mammals as demonstrated by their effect against leukemia L 1210 or P 388. In general, satisfactory results are obtained when the active compounds are administered intra-peritoneally in a single daily dose of from about 30 mg to about 80 mg/kg of mouse bodyweight. For such administration, the compounds can be formulated with physiologically inert liquids. In addition, the compounds of Formulas I and II are useful in studies to enhance activity and reduce toxicity of related compounds and as intermediates for exploration of additional active compounds.

There follow a number of Examples which are illustrative rather than limiting:

In the following Examples, melting points were determined on a Gallenkamp melting point apparatus and are uncorrected. Optical rotations are for chloroform solutions using a Perkin-Elmer 141 polarimeter. Infrared spectra were recorded on the Unicam SP1100 and the Beckman IR-20A spectraphotometers. Absorptions are reported in cm$^{-3}$ and are noted as strong (s), medium (m), weak (w) or broadened (br). $^{1}$H nmr spectra were obtained on Varian HA-100 and T-60 spectrometers. $^{13}$C nmr spectra were obtained on a Varian FT-80 spectrometer. All spectra were taken using deuterochloroform (CDCl₃) as solvent (unless otherwise indicated) and tetramethylsilane (TMS) as the internal standard. The chemical shifts are relative to the internal standard, TMS. The coupling patterns are noted as singlet (s), doublet (d), triplet (t), quartet (q), doublet of doublet (dd), doublet of triplets (dt), doublet of quartets (dq), broadened (br) or multiplet (m). Mass spectra were obtained on a AEIMS 9025 instrument.

Thin layer chromatography (TLC) was performed on Merck 60F 254 precoated silica plates of 0.25 mm thickness. Preparative thin layer chromatography (PTLC) was carried out on plates coated with a 0.5 mm layer of Kieselgel. Column chromatography was performed using silica gel (Baker 60–200 mesh) as the adsorbant. High performance liquid chromatography (HPLC) was carried out using PrepPak ®-500/silica cartridges on a Waters 500 instrument. Microanalyses were carried out by Canadian Microanalytical Service Ltd, Vancouver, B.C.

Tetrahydrofuran (THF) was always distilled over sodium/benzophenone under a nitrogen atmosphere immediately prior to use. All other solvents were distilled or of reagent grade quality.

Normal workup involved pouring the reaction mixture into water or saturated ammonium chloride solution, extracting three times with methylene chloride, drying the organic extracts with magnesium sulphate and evaporating the solvents on a rotary evaporator.

EXAMPLE 1

Preparation of the dianion of podophyllotoxin and subsequent reaction with methyl iodide Podophyllotoxin (207 mg, 0.5 mmol) was dissolved in a small volume of dry THF and added slowly to a cooled (−78° C.) solution of LDA (2 equivalents), prepared from diisopropylamine (0.29 ml) and n-BuLi (0.83 ml, 2.4M in hexanes) in 5 ml of dry THF. The yellow solution was stirred for 15 minutes at −78° and then excess CH₃I (0.25 ml) was added. The solution was warmed to room temperature and stirred for an additional 18 h. The usual workup followed by column chromatography on silica gel (hexanes/ethyl acetate; 1:1) afforded two components which were obtained as beige powders after precipitation from ether/hexanes. The major component (112 mg, 53%) was identified as 2-methylpicropodophyllotoxin, 142, and the minor component was identified as 2-methylpodophyllotoxin (40 mg, 18%), 143.

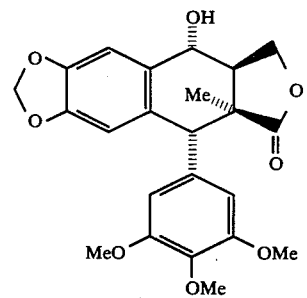

C₂₃H₂₄O₈ 428.42

Mp 92°–95° C.

IR (CHCl₃) ν$_{max}$ (cm$^{-1}$), 3300–3550 (br), 1770 (s), 1590 (s). $^{1}$H nmr δ (ppm) 1.12 (s, 3H), 2.79 (ddd, J=7.8, 6.0, 1.4 Hz, 1H), 3.79 (s, 6H), 3.80 (s, 3H), 4.23 (s, 1H), 4.57 (d, J=7.8 Hz, 1H), 4.42 (m, 2H), 6.94 (d, J=0.5 Hz, 1H), 6.96 (d, J=0.5 Hz, 1H), 6.65 (s, 1H), 6.76 (s, 1H), 6.78 (s, 2H).

M.S. m/e 428 (M+).

[α]$_D$ = −107.22 (CHCl₃) c=0.41

Analysis Calcd. for C₂₃H₂₄O₈: C, 64.48; H, 5.65. Found: C, 64.03, H, 6.22.

EXAMPLE 2

Preparation of 4-O-tetrahydropyranylpodophyllotoxin 144

The THP derivative of podophyllotoxin was prepared in 85% yield according to Gensler, *J. Org. Chem.*, 31: 4004 (1966), using freshly distilled dihydropyran with p-TsOH as the acid catalyst and CH₂Cl₂ as the solvent.

Preparation of the enolate anion of 144 and subsequent reaction with methyl iodide The THP derivative 144 (400 mg, 0.8 mmol) was dissolved in a small volume of dry THF and added slowly to a cooled solution (−78°) of LDA (one equivalent), prepared from diisopropylamine (0.23 ml) and n-BuLi (0.48 ml) in 10 ml of dry THF. The yellow solution was stirred for 15 minutes at −78° and then CH₃I was added (0.5 ml). The solution was warmed to room temperature and stirred for an additional 18 h. Normal workup afforded a viscous oil which was passed through a short silica gel column to remove any salts prior to hydrolysis to the THP group.

The crude methylation product was hydrolysed by refluxing in 10 ml of a solution of 5% aqueous Hcl and THF (1:9) for 4 h. Workup afforded a yellow foam that was separated into three components by HPLC (hexanes/ethyl acetate, 1:1). Each component was precipitated from ether/hexanes affording beige powders identified as the following in order of elution from the column: picropodophyllotoxin (20 mg, 6%), 2-methylpicropodophyllotoxin 142 (60 mg, 18%) and 2-methylpodophyllotoxin 143 (145 mg, 43%). 2-Methylpicropodophyllotoxin, 142 was identical in all respects to that product obtained via the dianion route.

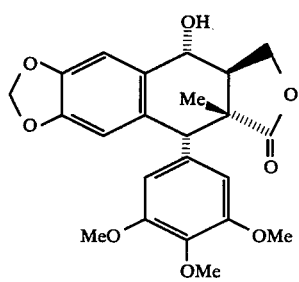

143
$C_{23}H_{24}O_8$
428.42

Mp 101°–103° C.

IR (CHCl$_3$) $\nu_{max}$ (cm$^{-1}$) 3350–3550 (br), 1780 (s), 1590 (s).

$^1$H nmr δ (ppm) 400 MHz, 1.32 (s, 3H), 2.89 (ddd, J=7.5, 10.5, 11.0 Hz, 1H), 3.75 (s, 6H), 3.81 (s, 3H), 4.17 (dd, J=9.0, 10.5 Hz, 1H), 4.26 (s, 1H), 4.51 (dd, J=7.5, 9.0 Hz, 1H), 4.70 (d, J=11.0 Hz, 1H), 5.98 (d, J=0.5 Hz, 1H), 5.97 (d, J=0.5 Hz, 1H), 6.36 (s, 1H), 6.36 (s, 2H), 6.48 (s, 1H), 7.10 (s, 1H).

$^{13}$C nmr δ (ppm) 22.50, 46.72, 48.74, 50.74, 56.24, 60.85, 72.02, 73.18, 101.29, 107.23, 107.93, 109.64, 129.27, 131.81, 135.87, 136.84, 147.37, 148.13, 152.42, 153.13, 180.83.

M.S. m/e 428 (M+).

[α]$_D$ (CHCl$_3$)=−118°, c=0.43

Analysis Calcd. for $C_{23}H_{24}O_8$: C, 64.48, H, 5.65; Found: C, 64.39, H, 5.61.

EXAMPLE 3

Trapping of the enolate anion prepared from 144 with oxygen

Treatment of 144 (498 mg, 1.0 mmol) with 1 equivalent of LDA in dry THF at −78° C. produced a clear yellow solution of the enolate anion that was trapped with oxygen by bubbling dry oxygen through the solution for 30 minutes. The solution was warmed to room temperature and stirred for an additional hour. The reaction mixture was treated with a saturated solution of sodium sulfite to reduce the intermediary hydroperoxides. Normal workup followed by hydrolysis of the crude product afforded a yellow foam which was purified by column chromatography on silica gel (hexanes/ethyl acetate; 1:1). Precipitation from either/hexanes furnished 350 mg (80%) of a colorless powder which was shown by nmr to be a 1:1 mixture of 2-hydroxypodophyllotoxin 146 and 2-hydroxypicropodophyllotoxin 147. These isomers were not separable.

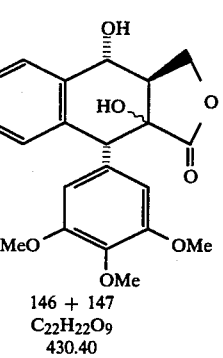

146 + 147
$C_{22}H_{22}O_9$
430.40

IR (CHCl$_3$) $\nu_{max}$ (cm$^{-1}$) 3300–3550 (br), 1775 (s), 1590 (s).

$^1$H nmr δ (ppm) 2.60–3.33 (m, 2H), 3.79+3.74 (s, 6H), 3.87+3.83 (s, 3H), 4.25 (m, 3H), 4.90 (m, 1H), 5.96 (br, 2H), 6.38+6.46 (s, 2H), 6.49+6.34 (s, 1H), 7.04+7.10 (s, 1H).

M.S. m/e 430 (M+).

Analysis Calcd. for $C_{22}H_{22}O_9$: C, 61.53; H, 4.93. Found: C, 61.59; H, 5.08.

EXAMPLE 4

Trapping of the enolate anion prepared from 144 with hexacloroethane

Treatment of 144 (249 mg, 0.5 mmol) with 1 equivalent of LDA in dry THF at −78° followed by trapping with excess hexachloroethane (178 mg) and warming of the solution to room temperature, stirring for an additional 18 h and normal workup afforded a viscous oil. The crude product was hydrolyzed in a mixture of 5% HCl and THF (1:9). The crude deprotected product was purified by column chromatography (hexanes/ethyl acetate, 1:1) affording only one product (164 mg, 74%) identified as 2-chloropodophyllotoxin, 148.

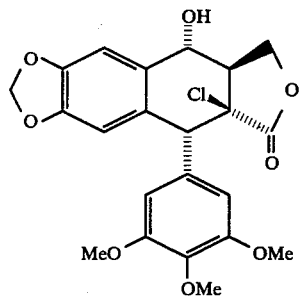

$C_{22}H_{21}O_8Cl$ 448.85

Mp 106°–110° C.

IR (CHCl$_3$) $\nu_{max}$ (cm$^{-1}$) 3300–3550 (br), 1785 (s), 1590 (s).

$^1$H nmr δ (ppm) 2.79 (d, 7.0 Hz, 1H), 3.07 (ddd, J–7.0, 9.0, 9.5, 1H), 3.77 (s, 6H), 3.84 (s, 3H), 4.26–4.65 (m, 2H), 4.79 (s, 1H), 4.98 (dd, J=7.0, 9.5 Hz, 1H), 5.97 (d, J=0.5 Hz, 1H), 5.99 (s, J=0.5 Hz, 1H), 6.44 (s, 2H), 6.49 (s, 1H), 7.09 (s, 1H).

M.S. m/e 448 (M+), 450 (M+2).

[α]$_D$ (CHCl$_3$)=−133.46 c=0.74.

Analysis Calcd. for $C_{22}H_{21}O_8Cl$: C, 58.86; H, 4.72. Found: C, 59.03; H, 4.98.

EXAMPLE 5

Isolation of 2-chloro-4-O-tetrahydropyranylpodophyllotoxin 149

Upon repeating the chlorination reaction the tetrahydropyranyl derivative, 149 was isolated by column chromatography (hexanes/ethyl acetate; 2:1) in 80% yield.

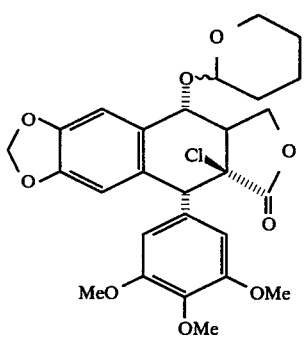

$C_{27}H_{29}O_9Cl$
532.96

IR (CHCl$_3$) $v_{max}$ (cm$^{-1}$) 1783 (s), 1590 (s).
M.S. m/e 532 (M$^+$), 534 (M+2).

EXAMPLE 6

Preparation of 4'-O-demethyl-2-chloro-1-O-(4,6-ethylidene-β-D-glucopyranosyl)-epipodophyllotoxin 150

4'-O-Demethyl-1-O-(4,6-ethylidene-β-D-glucopyranosyl)epipodophyllotoxin (VP16, 1.17 g, 2.0 mmol) was treated with 4 equivalents of LDA at −78° C. followed by hexachloroethane (2.37 g). The solution was warmed to room temperature and stirred for an additional 18 h. The tetra-anion was not very soluble under these reaction conditions. Workup consisted of washing with saturated sodium sulfite solution and extraction of the aqueous phase three times with CH$_2$Cl$_2$, drying and evaporation of the solvent. The crude product was purified by PTLC (hexanes/ethyl acetate; 1:3, 3 runs) affording starting material (800 mg, 70%) and a slightly more mobile compound (125 mg, 10%) identified as 4'-O-demethyl-2-chloro-1-O-(4,6-ethylidene-β-D-glucopyranosyl)-epipodophyllotoxin, 150.

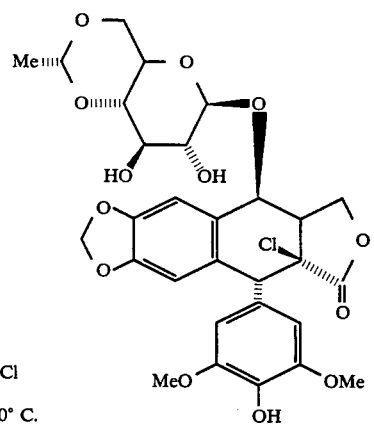

$C_{29}H_{31}O_{13}Cl$
623.00
Mp 155–160° C.

IR (CHCl$_3$) $v_{max}$ (cm$^{-1}$) 3300–3550 (br), 1780 (s), 1620 (s).

$^1$H nmr δ (ppm) 1.37 (d, J=5.0 Hz, 1H), 2.60 (s, 2×OH), 320 (m, 1H), 3.28–3.77 (m, 6H), 3.54 (s, 6H), 4.12 (dd, J=8.0, 5.0 Hz, 1H), 4.57 (dd, J=8.0, 7.0 Hz, 1H), 4.65 (dd, J=8.7, 8.0 Hz, 1H), 4.72 (s, 1H), 4.73 (q, J=5.0 Hz, 1H), 5.17 (d, J=3.0 Hz, 1H), 5.52 (s, phenolic OH), 5.98 (d, J=0.5 Hz, 1H), 6.00 (d, J=0.5 Hz, 1H), 6.58 (s, 2H), 6.75 (s, 1H), 7.04 (s, 1H).

M.S. m/e 623 (M$^+$), 6.25 (M+2).

[α]$_D$ (CHCl$_3$)= −59.35, c−1.30

Analysis Calcd. for $C_{29}H_{31}O_{13}Cl$: C, 55.91; H, 5.02. Found C, 56.02; H, 5.05.

EXAMPLE 7

Reaction of the enolate of 144 with Br$_2$

The tetrahydropyranyl derivative of podophyllotoxin, 144, 501 mg, 1.0 mmole, dissolved in 4 ml of dry THF was added to 5 ml of THF at −78° containing 1.1 mmole of LDA. The reaction mixture was stirred for 15 min. and then treated with 0.06 ml of Br$_2$, allowed to warm to room temperature over a 15 min. period and then quenched with 5 ml of saturated salt solution. The crude product was separated by plate chromatography using 3:1 hexane-ethyl acetate as eluent to yield 201 mg, 35%, of isomer I, mp 86°–89°, and 124 mg (21%) of isomer II, mp. 82°–85°.

The use of CBr$_4$ as brominating agent afforded 11% of isomer I and 33% of isomer II.

The isomers were hydrolyzed by refluxing with 10:1 THF −10% aqueous HCl for 1 hr. The yield of 2-brominated podophyllotoxin were 20 and 60% for isomer I and II, respectively.

Analysis: Calculated for $C_{22}H_{21}BrO_8$: C 53.56, H 4.29. Found: Isomer I mp 89°–93°: C 53.85, H 4.41. Isomer II mg 93°–98°: C 53.82, H 3.67.

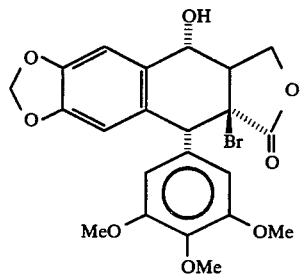

Isomer I

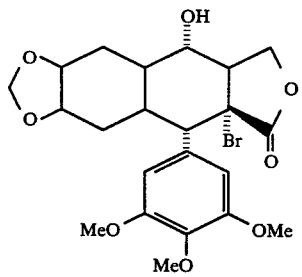

Isomer II

EXAMPLE 8

2-Chloroetoposide (Alternate Preparation)

A solution of 1.5 mmole of LDA in 10 ml THF and 3.4 ml of HMPA was prepared at 0° C. To this was added 200 mg (0.35 mmole) of Etoposide. The reaction mixture was stirred for 20 min. at 0°, treated with 660 mg (2.8 mmole) of hexachloroethane in 1.0 ml of THF and then stirred at room temperature for 22 h. Workup was affected by quenching with sat. (10 ml) ammonium chloride and then adding 10 ml of sat. Na₂SO₃ and then extracting 4× with CH₂Cl₂ (10 ml). The CH₂Cl₂ solution was dried and the solvents were evaporated first at 35° and then at 50°-80° using a rotovap to remove most of the HMPA. The crude product, 525 mg, was placed on 3 20×20 TLC plates and eluted with 75% ETOAc-25% hexane to afford 289 mg (43%) of a tan solid whose physical and spectroscopic properties were identical to that obtained via the tetra anion route.

EXAMPLE 9

Preparation of Disilylated Etoposide

Etoposide (250 mg, 0.425 mmole) (263 mg, 1.7 mmole) of chloro-t-butyldimethylsilane and 2.2 mmole (149 mg) of immidazole were heated in 3 ml of DMF at ~60° for 2 h. The reaction mixture was cooled and diluted with 15 ml of CH₂Cl₂ and 10 ml of hexane which gave a Ppte. The reaction mixture was filtered and the solution was washed 4× with H₂O, dried and evaporated to afford 503 mg of a clear oil. Chromatography on silica gel using 1:4 hexane-ethyl acetate afforded 231 mg of a white foam mp 90°-95° $C_{41}H_{60}O_{13}Si_2$(MW 817) Found: MS(FAB) 817.

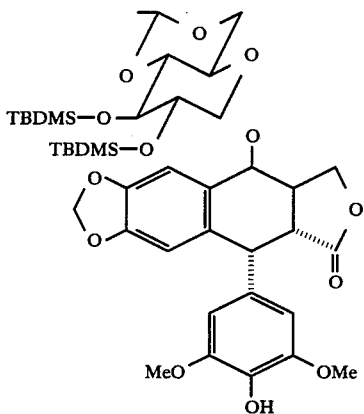

Methylation of Disilylated Etoposide

To a solution of 0.77 mmole of LDA in 10 ml of THF at −78° was added 300 mg 0.37 mmole of disilylated Etoposide in 1 ml of THF. The clear reaction mixture was stirred at −78° for 20 min. and treated with 1.3 ml (excess) of CH₃I. The solution was then stirred for a further 20 min. at −78° and then at room temp. overnight. Usual workup afforded 302 mg of a brown foam which was purified via silica gel plates using 20% EtoAc/hexane as eluent to yield 126 mg (41%) methylated product.

This material (126 mg) was disilylated by dissolving it in 10 ml of dry THF and added 0.44 ml of a 1M TBAF solution in THF. The reaction mixture was stirred for 40 min. at room temperature poured into sat. NH₄ Cl solution and worked up further in the usual way. The crude product, 113 mg of yellow solid was recrystallized from ethanol-hexane to yield 69 mg (75%) of a brown solid mp 180°-185°.

NW ($C_{30}H_{34}O_{13}$) Calcd: 602.57. Found: (FAB) 602.

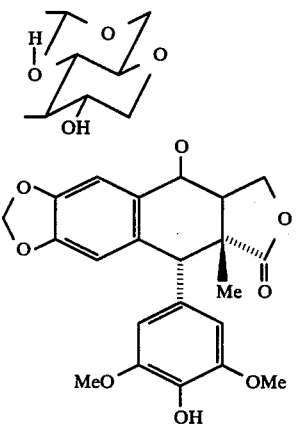

The following abbreviations have been employed herein:

n-BuLi: n-butyllithium
DCC: dicyclohexylcarbodiimide
DMF: dimethylformamide
h: hours
HMPT: hexamethylphosphoramide
HPLC: high performance liquid chromatography
IR: infrared
LDA: lithium diisopropyl amide
mp: melting point
M.S.: mass spectra
nmr: nuclear magnetic resonance
PTLC: preparative thin layer chromatography
rt: room temperature
THF: tetrahydrofuran
tlc: thin layer chromatography
TsOH: p-toluenesulfonic acid

What is claimed is:

1. A 2-substituted podophyllotoxin corresponding to the formula:

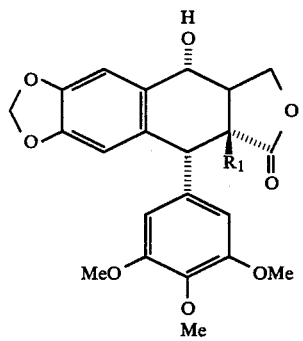

wherein $R_1$ is selected from the group consisting of halogen, lower alkyl, hydroxyl, and —$SR_5$ where $R_5$ is lower alkyl.

2. A 2-substituted Etoposides corresponding to the formula:

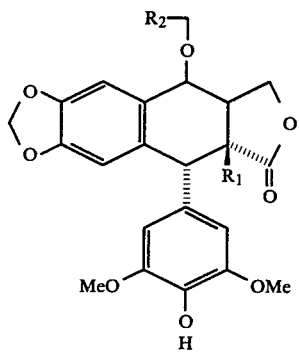

where $R_1$ is selected from the group consisting of halogen, lower alkyl, hydroxyl, and $-SR_5$ where $R_5$ is lower alkyl, and where $R_2$ is:

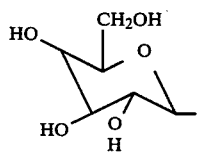

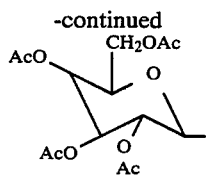

where AcO is acetyl; or

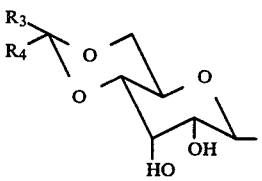

where $R_3$ is hydrogen and $R_4$ is alkyl, alkenyl, cycloalkyl, 2-furyl, 2-thienyl, aryl, or aralkyl, wherein the aromatic ring can be substituted by one or more hydroxyl, alkyl, alkoxy, nitro or halogen; or where $R_3$ and $R_4$ are both alkyl or where each of $R_3$ and $R_4$ taken together with the carbon atom to which they are attached signify a saturated cycloaliphatic ring having 5 or 6 carbon atoms; each alkyl, alkenyl or alkoxy above having no more than 10 carbon atoms and each aryl containing no more than 16 carbon atoms excluding substituents on the ring which are defined above.

3. 2-hydroxypodophyllotoxin.
4. 2-chloropodophyllotoxin.
5. 2-methylpodophyllotoxin.
6. 4′-O-demethyl-2-chloro-1-O-(4,6-ethylidine-β-D-glucopyranosyl)-epipodophyllotoxin.

* * * * *

UNITED STATES PATENT AND TRADEMARK OFFICE
CERTIFICATE OF CORRECTION

PATENT NO. : 4,567,253
DATED : January 28, 1986
INVENTOR(S) : TONY DURST ET AL.

It is certified that error appears in the above-identified patent and that said Letters Patent is hereby corrected as shown below:

Add to the U.S. Patent Documents under

References Cited:

--3,408,441 10/1968 von Wartburg et al. 536/18.1X 3,524,844 8/1970 Keller-Juslen et al. 536/18.1--.

Column 34, line 67 (claim 2, line 1), delete

"A" and change "2-substituted" to --2-Substituted--.

Signed and Sealed this

Fifteenth Day of April 1986

[SEAL]

Attest:

DONALD J. QUIGG

Attesting Officer    Commissioner of Patents and Trademarks